(12) United States Patent
Zemlok

(10) Patent No.: US 8,100,310 B2
(45) Date of Patent: Jan. 24, 2012

(54) VARIABLE COMPRESSION SURGICAL FASTENER APPARATUS

(75) Inventor: Michael A. Zemlok, Prospect, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 205 days.

(21) Appl. No.: 12/417,726

(22) Filed: Apr. 3, 2009

(65) Prior Publication Data

US 2009/0255977 A1   Oct. 15, 2009

Related U.S. Application Data

(60) Provisional application No. 61/044,689, filed on Apr. 14, 2008.

(51) Int. Cl.
*A61B 17/064* (2006.01)

(52) U.S. Cl. .................. 227/178.1; 227/19; 606/220

(58) Field of Classification Search ............ 227/176.1, 227/178.1, 19; 606/220; 411/469
See application file for complete search history.

(56) References Cited

U.S. PATENT DOCUMENTS

| | | |
|---|---|---|
| 1,756,670 A | 4/1930 | Treat |
| 3,258,012 A | 6/1966 | Nakayama et al. |
| 3,744,495 A | 7/1973 | Johnson |
| 3,771,526 A | 11/1973 | Rudie |
| 3,837,555 A | 9/1974 | Green |
| 4,014,492 A | 3/1977 | Rothfuss |
| 4,278,091 A | 7/1981 | Borzone |
| 4,319,576 A | 3/1982 | Rothfuss |
| 4,475,679 A | 10/1984 | Fleury, Jr. |
| 4,527,437 A | 7/1985 | Wells |
| 4,531,522 A | 7/1985 | Bedi et al. |
| 4,532,927 A | 8/1985 | Miksza, Jr. |
| 4,534,350 A * | 8/1985 | Golden et al. ............ 606/220 |
| 4,548,202 A | 10/1985 | Duncan |
| 4,573,469 A | 3/1986 | Golden et al. |
| 4,589,416 A * | 5/1986 | Green ....................... 606/220 |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,627,437 A | 12/1986 | Bedi et al. |
| 4,741,336 A | 5/1988 | Failla et al. |
| 4,767,044 A | 8/1988 | Green |

(Continued)

FOREIGN PATENT DOCUMENTS

EP    0 129 442    12/1984

(Continued)

OTHER PUBLICATIONS

European Examination Report mailed Sep. 20, 2010 in European Patent Application No. EP 09 251 793.7.

(Continued)

*Primary Examiner* — Rinaldi Rada
*Assistant Examiner* — Andrew M Tecco

(57) ABSTRACT

A surgical fastener applying apparatus comprising a fastener supporting portion and a retainer supporting portion. The fastener supporting portion includes a first row of first surgical fasteners and a second row of second surgical fasteners. The retainer supporting portion includes a first row of first retainers and a second row of second retainers, the first fasteners engagable with the first retainers and the second fasteners engagable with the second retainers. The fasteners and retainers are configured so when engaged a first distance between at least one of the first fastener backspans and respective first retainer backspan is different than a second distance between at least one of the second fastener backspans and respective second retainer backspan.

18 Claims, 10 Drawing Sheets

U.S. PATENT DOCUMENTS

| | | | |
|---|---|---|---|
| 4,805,617 A * | 2/1989 | Bedi et al. | 606/220 |
| 4,809,695 A | 3/1989 | Gwathmey et al. | |
| 4,848,637 A | 7/1989 | Pruitt | |
| 4,881,545 A | 11/1989 | Isaacs et al. | |
| 4,930,503 A | 6/1990 | Pruitt | |
| 4,932,960 A * | 6/1990 | Green et al. | 606/220 |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |
| 5,156,315 A * | 10/1992 | Green et al. | 227/178.1 |
| 5,156,614 A * | 10/1992 | Green et al. | 606/220 |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,253,793 A * | 10/1993 | Green et al. | 227/178.1 |
| 5,258,012 A * | 11/1993 | Luscombe et al. | 606/220 |
| 5,282,829 A * | 2/1994 | Hermes | 606/219 |
| 5,292,334 A * | 3/1994 | Howansky | 606/220 |
| 5,293,881 A * | 3/1994 | Green et al. | 128/898 |
| 5,342,396 A | 8/1994 | Cook | |
| 5,350,400 A | 9/1994 | Esposito et al. | |
| 5,352,229 A | 10/1994 | Goble et al. | |
| 5,352,238 A * | 10/1994 | Green et al. | 606/220 |
| 5,358,510 A * | 10/1994 | Luscombe et al. | 606/220 |
| 5,379,933 A * | 1/1995 | Green et al. | 227/176.1 |
| 5,425,489 A | 6/1995 | Shichman et al. | |
| 5,439,479 A | 8/1995 | Shichman et al. | |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A | 11/1995 | Rothfuss et al. | |
| 5,484,095 A | 1/1996 | Green et al. | |
| 5,497,931 A | 3/1996 | Nakamura | |
| 5,501,693 A | 3/1996 | Gravener | |
| 5,509,920 A | 4/1996 | Phillips et al. | |
| 5,571,116 A | 11/1996 | Bolanos | |
| 5,571,285 A | 11/1996 | Chow et al. | |
| 5,584,856 A | 12/1996 | Jameel et al. | |
| 5,620,452 A | 4/1997 | Yoon | |
| 5,634,926 A | 6/1997 | Jobe | |
| 5,653,373 A * | 8/1997 | Green et al. | 227/175.1 |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schutz | |
| 5,810,822 A | 9/1998 | Mortier | |
| 5,865,361 A | 2/1999 | Milliman et al. | |
| 5,871,135 A | 2/1999 | Williamson, IV et al. | |
| 5,879,371 A | 3/1999 | Gardiner et al. | |
| 5,915,616 A | 6/1999 | Viola et al. | |
| 5,961,521 A | 10/1999 | Roger | |
| 5,964,394 A | 10/1999 | Robertson | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,377,928 B2 | 5/2008 | Zubik et al. | |
| 7,398,908 B2 | 7/2008 | Holsten et al. | |
| 7,407,076 B2 | 8/2008 | Racenet et al. | |
| 7,455,676 B2 | 11/2008 | Holsten et al. | |
| 7,500,979 B2 | 3/2009 | Hueil et al. | |
| 7,547,312 B2 | 6/2009 | Bauman et al. | |
| 7,641,091 B2 | 1/2010 | Olson et al. | |
| 7,794,475 B2 | 9/2010 | Hess et al. | |
| 2002/0042621 A1 | 4/2002 | Liddicoat et al. | |
| 2004/0004105 A1 | 1/2004 | Jankowski | |
| 2004/0073222 A1 | 4/2004 | Koseki | |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales | |
| 2005/0023324 A1 | 2/2005 | Doll et al. | |
| 2005/0023325 A1 | 2/2005 | Gresham et al. | |
| 2005/0070925 A1 | 3/2005 | Shelton, IV et al. | |
| 2005/0070958 A1 | 3/2005 | Swayze et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ringl | |
| 2006/0049230 A1 | 3/2006 | Shelton, IV et al. | |
| 2006/0085030 A1 | 4/2006 | Bettuchi et al. | |
| 2006/0097026 A1 | 5/2006 | Shelton, IV | |
| 2006/0124688 A1 | 6/2006 | Racenet et al. | |
| 2006/0163312 A1 | 7/2006 | Viola et al. | |
| 2006/0226196 A1 | 10/2006 | Hueil et al. | |
| 2006/0291981 A1 | 12/2006 | Viola et al. | |
| 2007/0010838 A1 | 1/2007 | Shelton, IV et al. | |
| 2007/0034666 A1 * | 2/2007 | Holsten et al. | 227/176.1 |
| 2007/0131732 A1 | 6/2007 | Holsten et al. | |
| 2007/0262116 A1 | 11/2007 | Hueil et al. | |
| 2008/0078800 A1 | 4/2008 | Hess et al. | |
| 2008/0078804 A1 | 4/2008 | Shelton et al. | |

FOREIGN PATENT DOCUMENTS

| | | |
|---|---|---|
| EP | 0 169 044 | 1/1986 |
| EP | 0588081 A | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1 607 048 A1 | 12/2005 |
| EP | 1 785 098 | 8/2006 |
| EP | 1728473 A | 12/2006 |
| EP | 1 754 445 A2 | 2/2007 |
| EP | 1 875 868 | 1/2008 |
| EP | 1 917 918 | 5/2008 |
| EP | 2 095 777 | 9/2009 |
| FR | 2838952 | 10/2003 |
| GB | 2019296 A | 10/1979 |
| GB | 2 029 754 | 3/1980 |
| GB | 2029754 A | 3/1980 |
| GB | 2051287 A | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 | 6/1996 |
| WO | WO 97/34533 | 9/1997 |

| WO | WO 02/30296 A | 4/2002 |
| --- | --- | --- |
| WO | WO 03/094743 | 11/2003 |
| WO | WO 03/094747 | 11/2003 |
| WO | WO 2006/055385 A | 5/2006 |
| WO | WO 2008/007377 | 1/2008 |
| WO | WO 2008/039250 | 4/2008 |
| WO | WO 2008/089050 | 7/2008 |

OTHER PUBLICATIONS

European Search Report for EP 06016963.8-2318 date of completion is Mar. 9, 2007.

European Search Report mailed Nov. 16, 2009 in European Patent Application No. EP 09 251 793.7, filed Jul. 15, 2009.

European Search Report mailed Oct. 19, 2009 in EP Application No. 09251240.9 filed May 1, 2009.

International Search Report from EP Application No. 07 25 4366 dated Nov. 11, 2010.

International Search Report from EP Application No. 09 25 1067 mailed Mar. 17, 2011.

European Search Report EP08 25 2283 dated Jan. 15, 2009.

European Search Report EP09 25 1224.3-2310 dated Oct. 8, 2009.

European Search Report EP09 25 1268 dated Sep. 9, 2009.

European Search Report EP10251797 dated Jan. 31, 2011.

* cited by examiner

FIG. 10A  FIG. 10B

VARIABLE COMPRESSION SURGICAL FASTENER APPARATUS

This application claims priority from provisional application Ser. No. 61/044,689, filed Apr. 14, 2008, the entire contents of which are incorporated herein by reference.

BACKGROUND

1. Technical Field

The present disclosure relates to surgical fastener applying apparatus. More particularly, the present disclosure relates to a fastener applying assembly that includes a plurality of two-part surgical fasteners configured to apply varying compressive forces to tissue.

2. Background of the Related Art

Many varieties of surgical fastening apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. U.S. Pat. Nos. 5,915,616, 6,202,914, 5,865,361, and 5,964,394 each describe one or more suitable apparatus which may be employed while performing one of these procedures.

In general, a surgical fastening apparatus will include an anvil that is approximated relative to a fastener cartridge during use or a fastener cartridge that is approximated relative to an anvil. The anvil includes depressions that are aligned with, and/or are in registration with slots defined in the cartridge, through which the fasteners will emerge, to effectuate formation. In other apparatus, the anvil contains a plurality of retainers with apertures to receive legs of the fasteners. The fastener cartridge typically has one or more rows of fasteners disposed laterally or radially of a channel that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and connected by a backspan from which they extend. In use, subsequent to formation, some of the unitary fasteners have a "B" configuration. Typically, the two-part fasteners include legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable and are generally made of a bioabsorbable material.

During each of the aforementioned surgical procedures, the tissue is initially gripped or clamped between the cartridge and anvil such that individual fasteners can be ejected from the cartridge, through the slots, and forced through the gripped tissue. Thereafter, the fasteners are formed by driving them into the depressions formed on the anvil or into the apertures of the retainers.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing.

Additionally, when tissue is clamped and compressed between the anvil and cartridge, some of the fluid of the tissue is squeezed out so the tissue is compressed further at the center portions of the cartridge and anvil than at the lateral edges, thereby leaving thicker tissue at the edges. It would therefore be advantageous to provide staples which could better accommodate these resulting different tissue thicknesses.

SUMMARY

The present disclosure provides in one aspect a surgical fastener applying apparatus comprising a fastener supporting portion and a retainer supporting portion. The fastener supporting portion includes a first row of first surgical fasteners and a second row of second surgical fasteners. The retainer supporting portion includes a first row of first retainers and a second row of second retainers, the first fasteners engagable with the first retainers and the second fasteners engagable with the second retainers. The first fasteners each have a first fastener backspan and the second fasteners each have a second fastener backspan, and the first retainers each have a first retainer backspan and the second retainers each have a second retainer backspan. The fasteners and retainers are configured so that when engaged a first distance between at least one of the first fastener backspans and respective first retainer backspan is different than a second distance between at least one of the second fastener backspans and respective second retainer backspan.

Preferably, the first row of fasteners is positioned inboard of the second row of fasteners and the first distance is less than the second distance. The apparatus may also include a third row of third fasteners and a third row of third retainers, wherein the third row of fasteners is positioned outboard of the second row of fasteners and the second distance is less than a distance between a backspan of at least one of the third fasteners and a backspan of a respective third retainer.

In some embodiments, the backspan of at least one of the first fasteners has a greater height than the backspan of at least one of the second fasteners, the first row of fasteners being positioned closer to a central longitudinal axis of the fastener supporting portion than the second row of fasteners. In some embodiments, the backspan of at least one of the first retainers has a greater height than the backspan of at least one of the second retainers, and the first row of retainers is positioned closer to a central longitudinal axis of the retainer supporting portion than the second row of retainers.

The apparatus may further include a third row of third fasteners and a third row of third retainers, wherein the third row of fasteners is positioned further from the central longitudinal axis than the second row of fasteners, and a height of a backspan of at least one of the third retainers is less than a height of the backspan of at least one of the second retainers.

In some embodiments, the retainer supporting portion and fastener supporting portion are pivotally attached. In other embodiments, at least one of the retainer supporting portion and fastener supporting portion is movable along a substantially linear path to move the retainer supporting portion and fastener supporting portion into approximation.

The first and second rows of fasteners can be arranged in a substantially annular configuration. The first and second rows of fasteners can also be arranged in a substantially linear configuration.

The present disclosure provides in another aspect a surgical fastener applying apparatus comprising a fastener assembly having a first pair of first rows of fasteners and a second pair of second rows of fasteners and a corresponding first pair of rows of retainers and a second pair of rows of retainers to receive the respective fasteners. At least one of the fasteners and retainers of the first pair of rows of fasteners and retainers is configured so when engaged applies a first compressive force on tissue and at least one of the fasteners and retainers of the second pair of rows of fasteners and retainers is configured so when engaged applies a second different compressive force on tissue.

Preferably the first pair of rows of fasteners is positioned closer to a central longitudinal axis of the fastener assembly and the first compressive force is greater than the second compressive force. In a preferred embodiment, a distance between the fastener backspan and retainer backspan is less in a plurality of fasteners in the first fastener row than in a plurality of fasteners in a second fastener row.

The present disclosure provides in another aspect a surgical fastener applying cartridge and anvil assembly for use with a surgical fastener applying instrument. The cartridge and anvil assembly include a cartridge having a first pair of rows of fasteners and a second pair of rows of fasteners and the anvil assembly includes a first pair of rows of first retainers and a second pair of rows of second retainers to receive the respective fasteners. At least one of the fasteners and retainers of the first pair of rows is configured so when engaged applies a first compressive force on tissue and at least one of the fasteners and retainers of the second pair of rows is configured so when engaged applies a second different compressive force on tissue.

Preferably, the first pair of rows of fasteners is positioned closer to a central longitudinal axis of the fastener assembly and the first compressive force is greater than the second compressive force. Preferably, a distance between the fastener backspan and retainer backspan is greater between at least one of the fasteners and retainers in the second row than between at least one of the fasteners and retainers in the first row.

BRIEF DESCRIPTION OF THE DRAWINGS

Various embodiments of the present disclosure are described hereinbelow with references to the drawings, wherein:

FIGS. 10A-10C illustrate the two-part surgical fastener depicted in FIG. 9 shown with the retainer having three different backspan configurations and being shown subsequent to formation (engagement with the fastener);

DETAILED DESCRIPTION OF EXEMPLARY EMBODIMENTS

Figure 1:
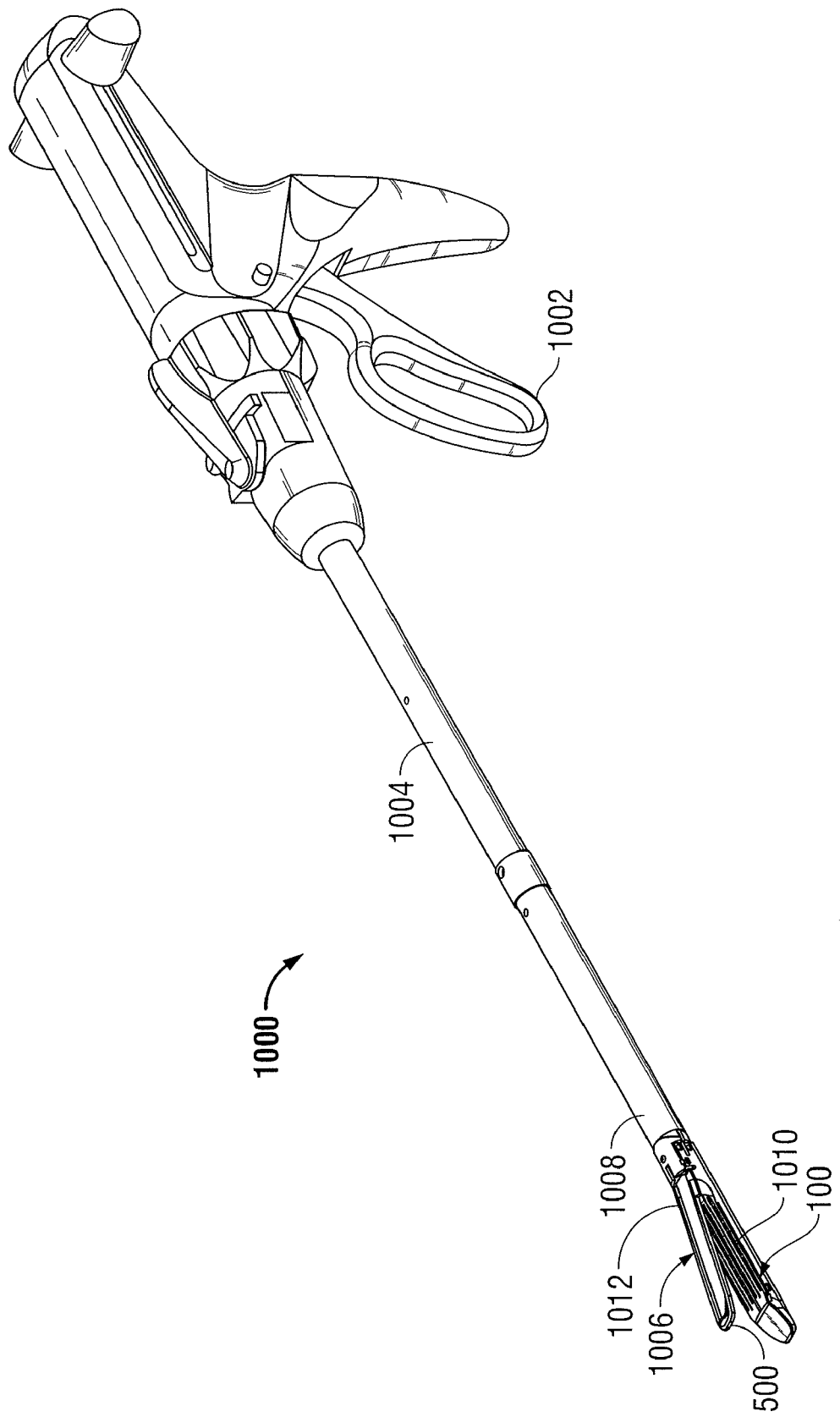
FIG. 1 illustrates an exemplary surgical fastener applying apparatus for use with a fastener applying assembly that employs a two-part surgical fastener in accordance with embodiments of the present disclosure.

Various exemplary embodiments of the presently disclosed surgical fastener applying assembly will now be described in detail with reference to the drawings wherein like references numerals identify similar or identical elements. In the drawings and in the description which follows, the term "proximal" will refer to the end of the surgical fastener cartridge that is closer to the operator during use, while the term "distal" will refer to the end of the fastener cartridge that is further from the operator, as is traditional and conventional in the art. In addition, the term "surgical fastener" should be understood to include any substantially rigid structure formed of a biocompatible material that is suitable for the intended purpose of joining tissue together, including but not being limited to fasteners engaging retainers, surgical staples, clips, and the like.

The present disclosure provides a fastener applying assembly adapted to house a plurality of two-part surgical fasteners providing varying degrees of compressive force to fastened tissue occupied therein such that an effective hemostatic effect at or near the cut-line may be achieved. To this end, the two-part surgical fasteners are configured such that the two-part surgical fasteners deployed closer to the cut line produce a greater compressive force to fastened tissue than the surgical fasteners deployed further from the cut line.

As noted, two-part fasteners typically include a fastener and a retainer to which the fastener is deployed into. The preferred fastener and retainer are composed of a bioabsorbable polymeric material, such as polymers or copolymers of glycolide, lactide, p-dioxanone, polyester, polyamino acids and the like, the preferred construction of which is shown and described in U.S. Pat. No. 4,932,960, which is hereby incorporated by reference.

With reference initially to FIG. 1, one type of surgical fastener applying apparatus 1000 that employs a fastener applying assembly 1006 is illustrated. Surgical fastener applying apparatus 1000 is used to sequentially apply a plurality of surgical fasteners to a patient's tissue. Surgical fastener apparatus 1000 may be configured for use, subsequent sterilization and reuse, although it is preferably configured for single use. Surgical fastener applying apparatus 1000 includes a handle 1002, an elongated shaft or endoscopic portion 1004 extending distally therefrom, and an assembly 1006 coupled to a distal end 1008 of the elongated shaft 1004. In general, assembly 1006 is adapted to clamp, sequentially fasten together, and sever adjacent tissue segments along a cut-line. Assembly 1006 includes a pair of opposed jaws 1010, 1012 pivotally coupled to one another and respectively including an anvil member or retainer supporting portion 500 that is approximated relative to a surgical fastener cartridge or fastener supporting portion 100 during use. The retainer supporting portion 500 includes retainers that are aligned in registration with slots 126 defined in the cartridge 100, through which a surgical fastener 130 will emerge, to effectuate formation as it engages the retainer. For a more detailed discussion of the approximation and firing of surgical fastener applying apparatus 1000, reference is made to commonly owned U.S. Pat. No. 5,865,361, currently assigned to Tyco Healthcare Group LP, the entire contents of which is incorporated herein by reference. In preferred embodiments, cartridge 100 containing the fasteners and anvil 500 containing the retainers are removable and replaceable with another loaded cartridge and anvil.

Figure 2:
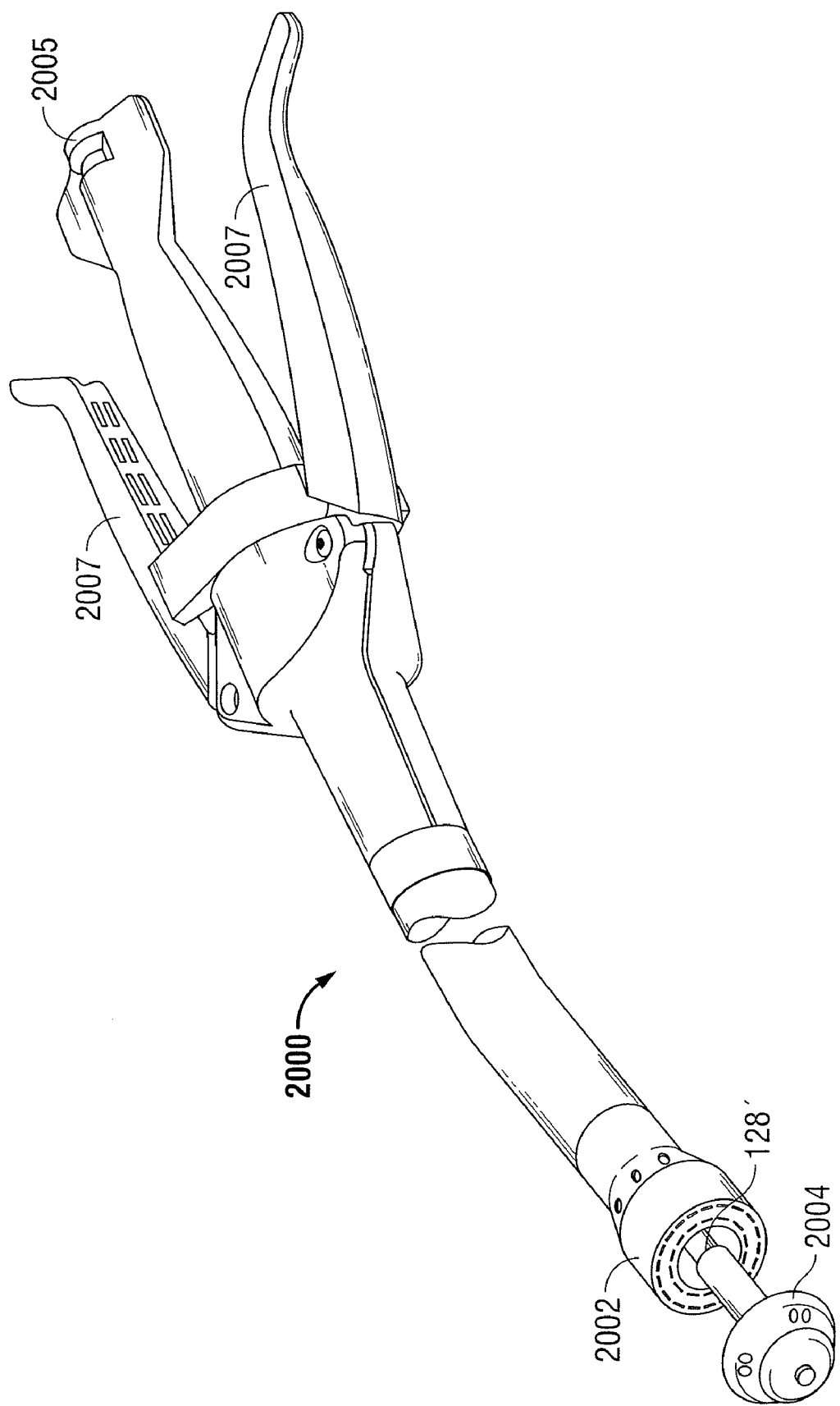
FIG. 2 illustrates another type of surgical fastener apparatus that may employ an alternate embodiment of a fastener applying assembly in accordance with the present disclosure.
Figure 3:
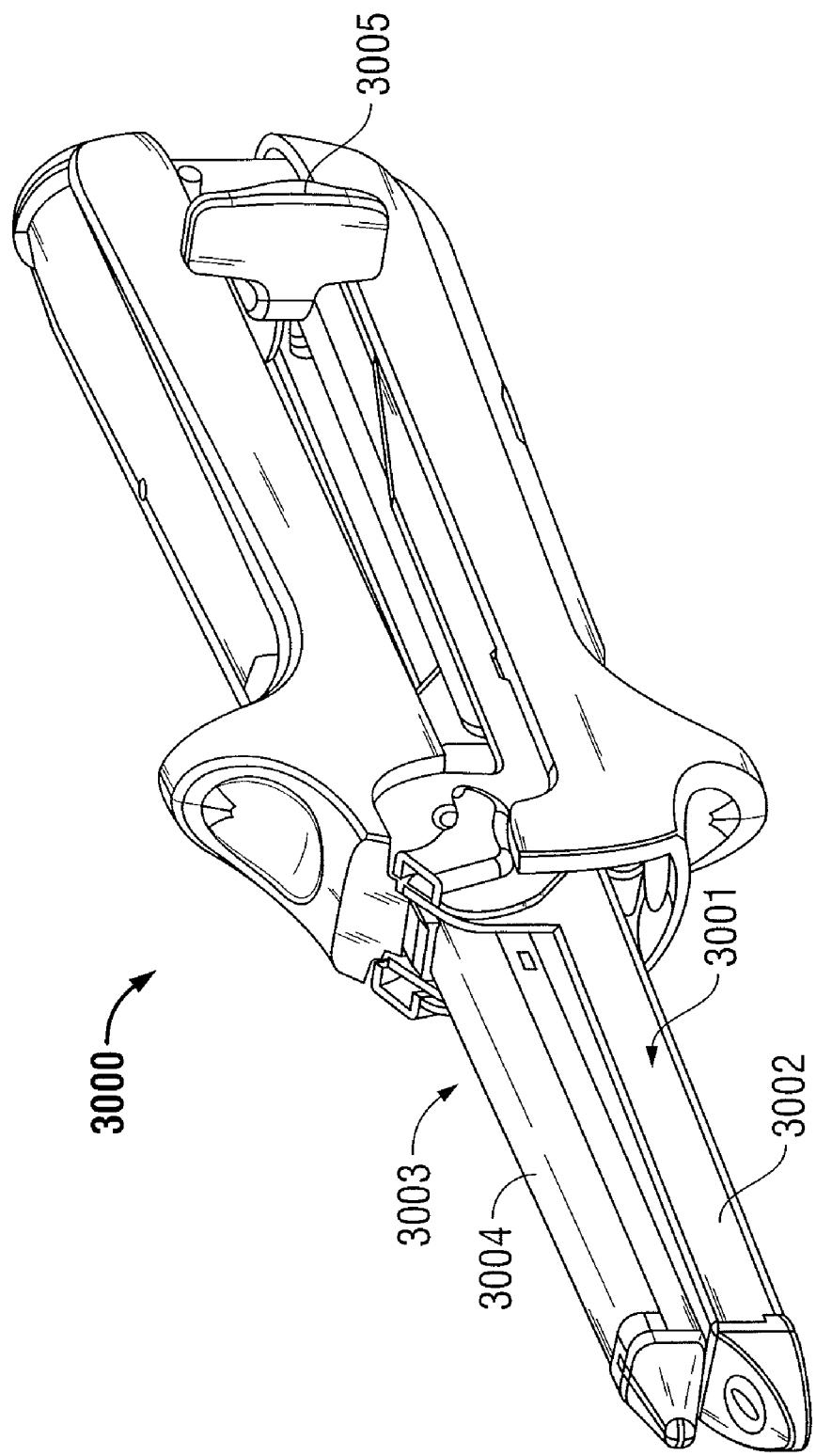
FIG. 3 illustrates another type of surgical stapling apparatus that may employ an alternate embodiment of fastener applying assembly in accordance with the present disclosure.

While assembly 1006 is depicted as an apparatus suitable for use in laparoscopic procedures for performing surgical anastomotic fastening of tissue, those skilled in the art will appreciate that cartridge 100 and retainer supporting portion 500 may be adapted for use with any surgical instrument suitable for the intended purposes described herein. For example, assembly 1006 may be adapted for use with an end-to-end anastomosis device 2000, as seen in FIG. 2, wherein the fasteners and retainers are arranged in substantially annular rows and/or a surgical stapling instrument 3000, as seen in FIG. 3, for use during an open gastro-intestinal anastomotic stapling procedure wherein the fasteners and retainers are arranged in substantially linear rows, or, for example, any of the surgical fastener applying apparatus discussed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each incorporated by reference herein in their entirety.

For the purposes of brevity, the structural and operational features of assembly 1006 will be described in terms of use with the surgical fastener applying apparatus 1000.

Figure 4:
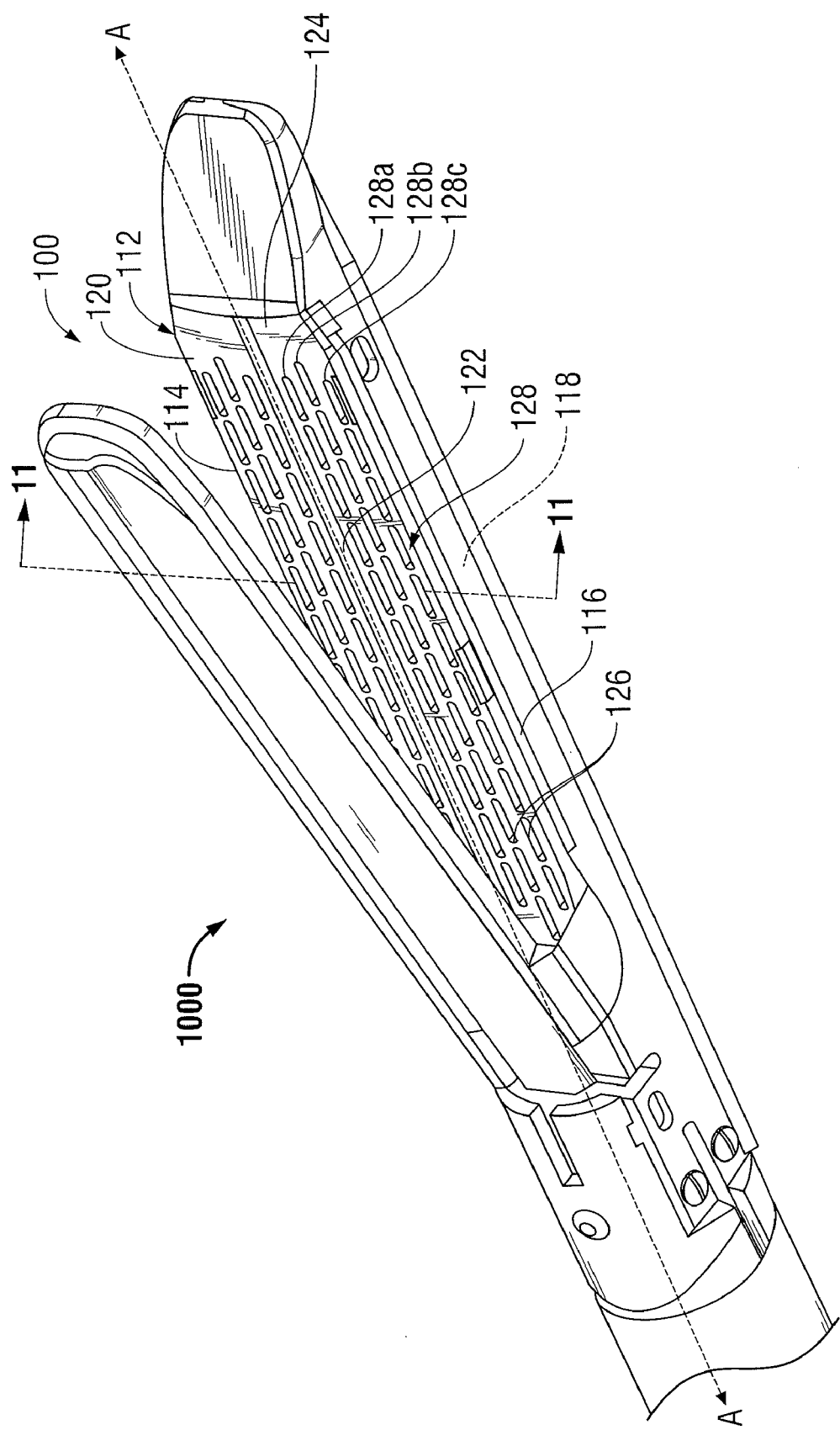
FIG. 4 is a perspective view of fastener applying assembly shown in the distal end portion of the surgical fastener apparatus depicted in FIG. 1.

With reference to FIG. 4, cartridge 100 of assembly 1006 is shown. Cartridge 100 extends along a longitudinal axis "A-A" and includes a cartridge body 112 with a pair of side walls 114, 116, a bottom wall 118, and a top wall 120. The top wall 120 includes a channel 122 that is configured to accommodate longitudinal movement of a knife (not shown), or other suitable cutting element, such that fastened tissue may be severed along a cut-line. The top wall 120 further includes a tissue engaging surface 124 (e.g., for maintaining the position of the tissue to be cut) and a plurality of fastener retention slots 126 arranged into a plurality of substantially linear rows 128. As shown in FIG. 4, the fastener retention slots 126 are arranged into a pair of first (inner) rows $128_A$ that are spaced laterally from the channel 122 and on opposite sides thereof, a pair of second (middle) rows $128_B$ that are spaced laterally (outboard) from the pair of first rows $128_A$ and on opposite sides of the channel 122, and a pair of third (outer) rows $128_C$ that are spaced laterally (outboard) from the pair of second rows $128_B$ and on opposite sides of channel 122. Rows $128_A$, $128_B$, and $128_C$ are in alignment and/or vertical registration with a plurality of corresponding rows 428 of anvil 500, to be described in greater detail below. While the cartridge 100 is depicted as including pairs of first, second, and third rows $128_A$, $128_B$, $128_C$, respectively, it is within the purview of the present disclosure to have more or fewer rows of the fasteners (and corresponding rows of retainers). Additionally, rows of fasteners (and corresponding rows of fastener retainers) may extend radially from the cutting element arranged in substantially annular rows, such is the case when the surgical fastening assembly is employed with the surgical fastening device depicted in FIG. 2.

Figure 11:
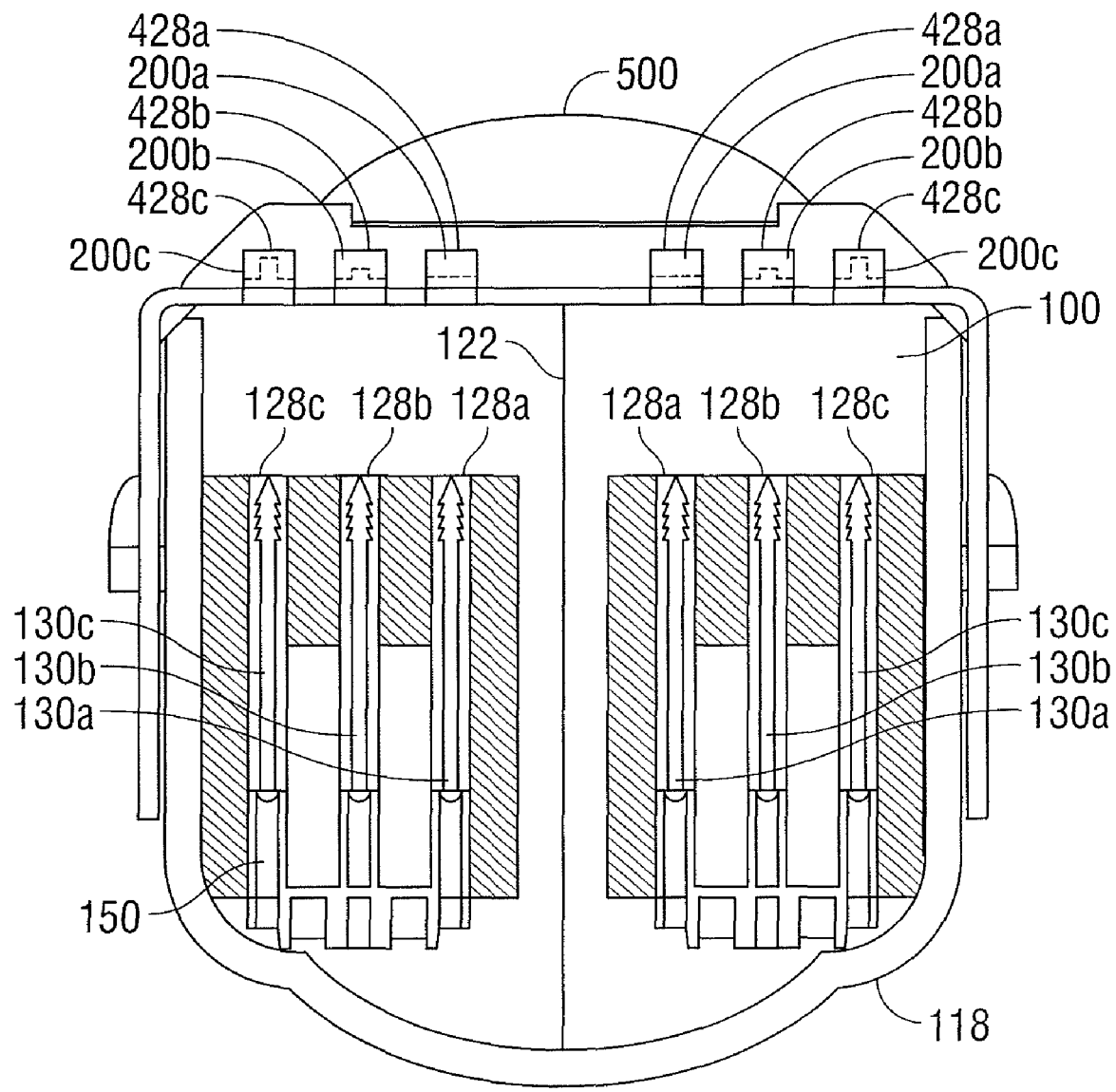
FIG. 11 is a partial cross-sectional view taken along the line segment "11-11" in FIG. 4 illustrating the fastener applying assembly loaded with the two-part surgical fastener depicted in FIGS. 10A-10C.

Each of the fastener retention slots 126 is configured to receive one of a plurality of surgical fasteners 130 and pushers 150 therein such that the surgical fasteners 130 are deployed in rows (e.g., inner, middle, and outer rows) on opposite sides of the cut-line created in the tissue during fastening, as shown in FIG. 11.

For a more detailed description of the functional and structural features of cartridge 100, reference is made to commonly owned U.S. Pat. Nos. 5,653,373 and 5,573,169 the disclosures of which are incorporated by reference herein.

With reference now to FIGS. 5, 6 and 7A-7D, cartridge 100 is loaded with one or more varieties of surgical fastener 130, represented generally as surgical fastener 130. Surgical fastener 130 of cartridge 100 is configured such that the surgical fastener 130 deployed closer to the cut line provides a greater compressive force to the fastened tissue than the surgical fastener 130 deployed further from the cut line. To this end, surgical fastener 130 includes two legs 132 connected by a backspan 134 extending therebetween with the thickness of backspan 134 varied such that the surgical fastener 130 closer to the cut line provides a greater compressive force to fastened tissue occupied therein than the surgical fastener 130 further from the cut line. The thickness of the legs 132 can also be varied to this end. The thickness of the backspan 134 and the thickness of the legs 132 may also be varied to fasten adjacent tissue segments "$T_1$", "$T_2$" of varying thickness.

Figure 6:
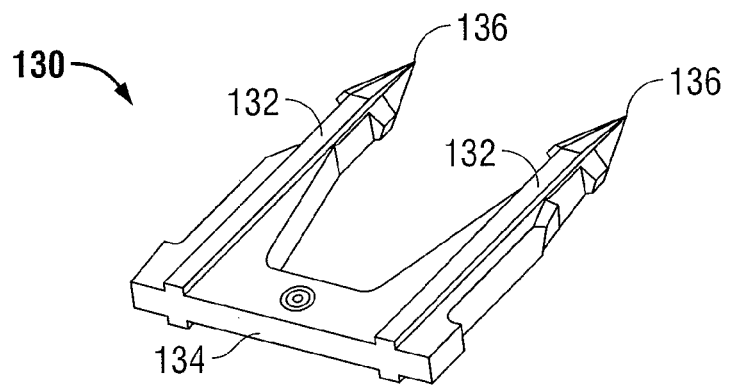
FIG. 6 is a side perspective view of a surgical fastener portion of a two-part surgical fastener configured for use with the fastener applying assemblies depicted herein.

The legs 132 and the backspan 134 may define a cross-section having any suitable geometric configuration, including but not limited to rectangular, oval, square, triangular, and trapezoidal. The legs 132 and the backspan 134 may exhibit the same geometrical configuration such that the cross-sectional configuration of the surgical fastener 130 is substantially uniform, as shown in FIG. 6, or, alternatively, the legs 132 and the backspan 134 may exhibit different geometrical configurations, e.g., the legs 132 may exhibit a rectangular cross-section and the backspan 34 may exhibit an oval cross-section, as shown in FIGS. 7A-7D, discussed in more detail below. Backspan 134 and/or legs 132 may be formed by any suitable methods known in the art including but not limited to welding, braising, coining, casting, molding, overmolding and so on. Additionally, backspan may include different configurations of blocking and/or retainer material, tube, sleeve, collar, and/or grommet.

Figure 5:
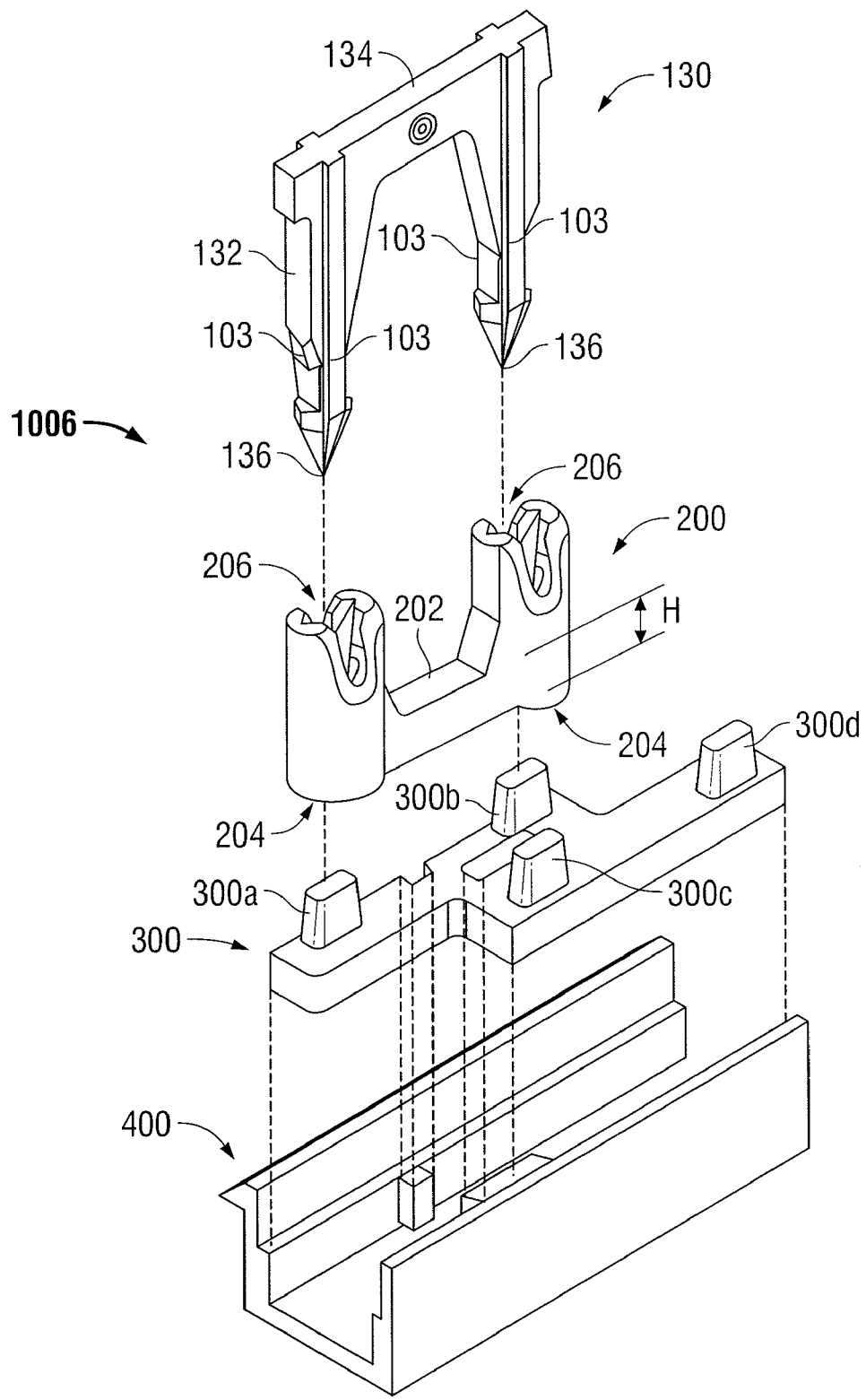
FIG. 5 is a partially exploded perspective view of a two-part surgical fastener configured for use with the fastener applying assemblies depicted herein.

As seen in FIGS. 5 and 6, legs 132 of the fastener extend from the backspan 134 such that they are substantially parallel. Alternatively, the legs 132 may converge or diverge from the backspan such that they are positioned at an acute or obtuse angle with respect to the backspan.

Each of the legs 132 preferably terminates in a generally spear shaped penetrating end 136 that is configured to penetrate tissue (tissue segments "$T_1$", "$T_2$" for example) and/or other suitable material (retainer material for example). Penetrating end 136 is dimensioned for forced entry into a pair of apertures 206 of a retainer 200, to be described in greater detail below. The penetrating ends 136 of legs 132 can be tapered to facilitate the penetration of tissue segments "$T_1$", "$T_2$", or alternatively, the penetrating ends 136 may not include a taper. In some embodiments, penetrating ends 136 may define a conical or flat surface. In various embodiments, one or both of legs 132 may be barbed, as best seen in FIGS. 9, 10A-10C, and 11 for example. Having legs 132 configured in such a manner may facilitate maintaining the surgical fastener 130 in a fixed position within retainer 200. Located on one or both of legs 132 may be one or more raised bumps 103 (FIG. 5). Bumps 103 are configured to help retain fastener 130 within retainer 200 after entry has been completed. While bumps 103 are shown at two locations, bumps 103 may also be provided on a rear face of fastener 130 (not shown) to retain the fastener.

As noted, retainers 200 are configured for joining with surgical fasteners 130 upon firing of the surgical fastener 130. With this purpose in mind, the retainers 200 are each positioned within the plurality of retainer rows 428 opposite the plurality of fastener rows 128 when the assembly 1006 is assembled, as best seen in FIG. 11.

With reference back again to FIG. 5, retainer 200, a retainer holder 300 and a retainer holder cartridge 400 of anvil 500 are shown. Retainer 200 includes a backspan 202, having a height "H", extending between retainer legs 203, and is securely positioned on retainer holder 300. Retainer holder 300 includes one or more upstanding posts 300a, 300b, 300c, and 300d which are dimensioned and configured to enter apertures 204 of retainer 200 on the side opposite the fastener 130 entry side. Each retainer holder 300 supports two retainers 200. The upright posts 300a, 300b, 300c and 300d each have a sloped side which is angled slightly off the vertical such that the top of the upright post is slightly narrower than the bottom. The tapering facilitates the entry and removal of the upright posts from retainer apertures 206. The retainer holder 300 provides a stable flat base for retainer 200 and disengages from the retainer 200 when fastener portion 130 engages the retainer 200. During operation, fasteners 130 are deployed from cartridge 100 to mate with their respective retainers 200.

Retainer holder 300 is operatively connected to a retainer holding cartridge 400. Retainer holding cartridge 400 is an elongated generally arcuately shaped piece that is adapted to hold retainer holders 300 in a frictional fitting such that they are frictionally supported in an initial upper position wherein the retainer holders 300 are engaged with the retainers 200. In some embodiments, the retainer holders 300 may be slightly curved along their sides to match the curvature of the cartridge 400 so as to be downwardly slidable when forced out of engagement with the retainers 200 by the entering tips 136 of the fastener 130.

Figure 8A:
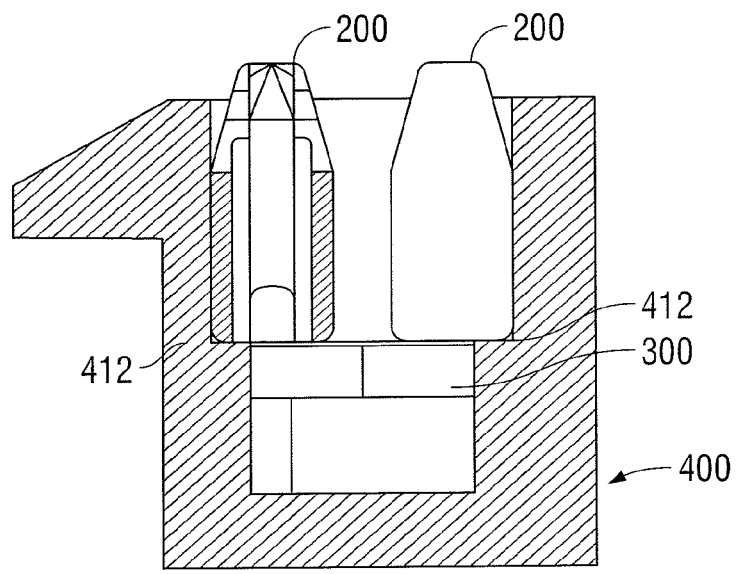
FIG. 8A illustrates in cross-sectional view a retainer portion of a two-part surgical fastener positioned on a retainer mounting element configured for use with the fastener applying assemblies depicted herein shown prior to engagement with the fastener.

Retainers 200 are initially in the position illustrated in FIG. 8A. Retainer 200 is located on the upper chamber of retainer holding cartridge 400, and mounted on retainer holder 300 by means of the posts which are inserted into the apertures 204 (FIG. 5) at the bottom of the retainer 200. A portion of the bottom of the retainer 200 overlaps the edge of base 302 such that the overlapping portion rests on a shelf 412 of retainer holding cartridge 400 (FIG. 8A).

Figure 8B:
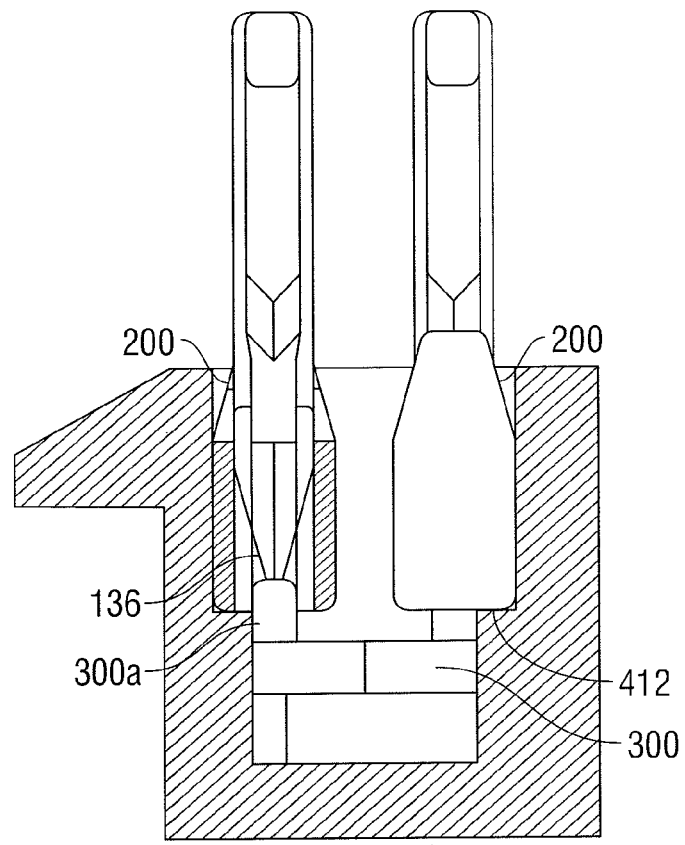
FIG. 8B illustrates in cross-sectional view, the retainer portion of a two-part surgical fastener depicted in FIG. 8A positioned on the mounting element shown subsequent to formation (engagement with the fastener)

Turning now to FIG. 8B, a surgical fastener 130 and a retainer 200 are shown subsequent to entry. When the fasteners 130 are inserted into retainers 200, the barbed tips 136 of the fasteners push down on the upright posts, e.g., post 300a, thereby pushing the retainer mounting element 300 down into a position where it is no longer in engagement with the retainer 200. The retainers 200 are dimensioned and configured to be supported by shelves 412 such that they are braced against downward movement. Upon disengagement with the retainer holders 300, the retainers 200 are free to be lifted out of the cartridge 400 in engagement with the fasteners. Reference is made to commonly assigned U.S. Pat. No. 5,653,373 for a more detailed description of the structural and operative features of the retainer 200, retainer holder 300 and retainer holder cartridge 400 of anvil 500.

Figure 9:
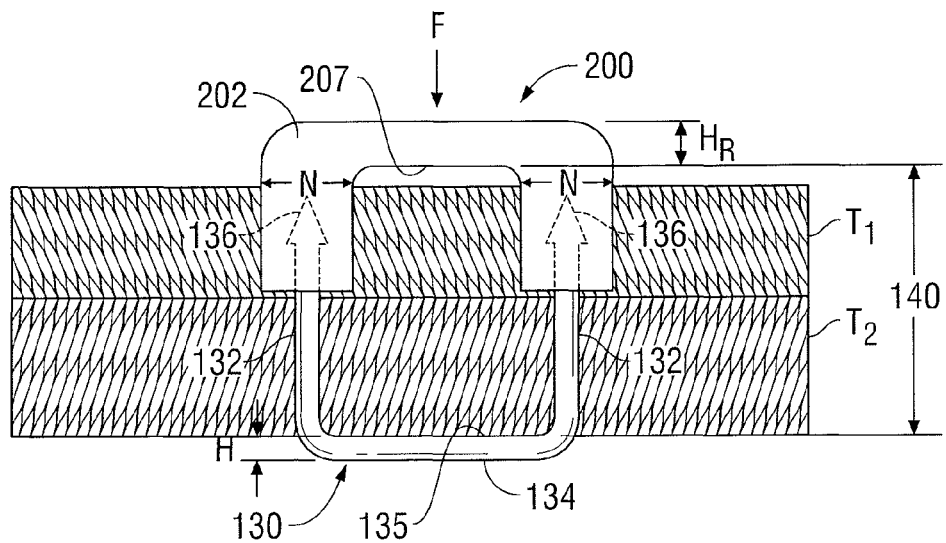
FIG. 9 is a side perspective view of the two-part surgical fastener depicted in FIG. 5 subsequent to formation (engagement) and within adjacent tissue segments.

With reference to FIG. 9, surgical fastener 130 and retainer 200 are shown subsequent to entry/engagement (or formation) with adjacent tissue segments occupied therein. As noted, the two-part surgical fastener includes surgical fastener 130 and retainer 200 configured to provide a compressive force to fastened tissue occupied therein i.e. in the space between the backspan 202 of retainer 200 and the backspan 134 of fastener 130. To this end, surgical fastener 130 cooperates with retainer 200 to maintain adjacent tissue segments "$T_1$", "$T_2$" in approximation and apply a compressive force "F" thereto. The compressive force "F" applies pressure to the tissue segments "$T_1$", "$T_2$", thereby restricting the flow of blood through the tissue surrounding the surgical fastener 130 and retainer 200 and facilitating hemostasis. The configuration of the backspan 134 of surgical fastener 130 and the retainer 200 may limit the amount of pressure that can be applied to the tissue segments "$T_1$", "$T_2$" such that the flow of blood through the tissue is not completely restricted. When joined, the surgical fastener 130 and retainer 200 will form an enclosure that has an overall tissue compression space 140, defined between the inner surface 135 (or upper surface as viewed in the orientation of FIG. 9) of the backspan 134 of the fastener 130 and the inner surface 207 (or lower surface as viewed in the orientation of FIG. 9) of the backspan 202 of the retainer 200.

Figure 10C:
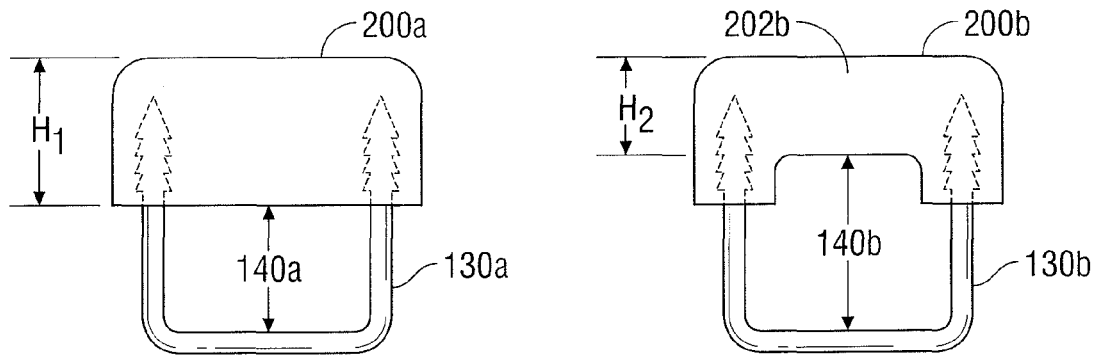
Figure 10C:
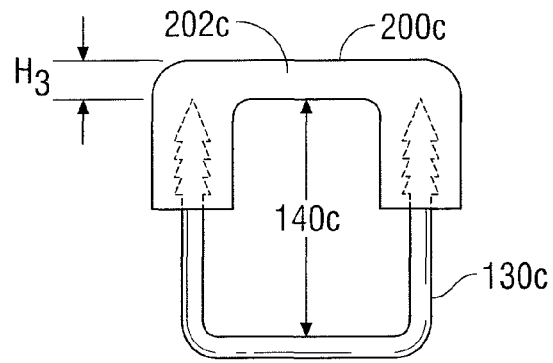

With reference to FIGS. 10A-10C, surgical fastener 130 will be described in terms of surgical fasteners $130_A$, $130_B$, and $130_C$, and retainer 200 will be described in terms of retainers $200_A$, $200_B$, and $200_C$. Surgical fasteners $130_A$, $130_B$, and $130_C$ and their respective retainers $200_A$, $200_B$, and $200_C$ are shown in their formed (or fully joined/engaged) conditions. Surgical fasteners $130_A$, $130_B$, $130_C$, are preferably substantially similar to each other; however, the retainers $200_A$, $200_B$, and $200_C$ differ as described below. Alternatively, surgical fasteners $130_A$, $130_B$, $130_C$ may have varying height backspans. These varying height fastener backspans can be provided in addition to the varying height retainer backspans or instead of the varying height retainer backspans. Having the surgical fasteners 130 and/or retainers 200 configured in such a manner with varying backspans may increase hemostasis of fastened tissue when the two-part fastener is formed.

The overall heights of the joined fasteners $130_A$, $130_B$, $130_C$ and respective retainers $200_A$, $200_B$, and $200_C$ (measured from the outer surface of the retainer backspan 202 to the outer surface of the fastener backspan 134) are preferably substantially the same, however, the compression spaces vary due to the variations in the retainer backspan. That is, the respective dimensions "$H_1$", "$H_2$", and/or "$H_3$" of backspan $202_A$, $202_B$, $202_C$ of retainer $200_A$, $200_B$, and $200_C$, may be altered, which, in turn, may alter the dimensions of the compression spaces $140_A$, $140_B$, $140_C$ occupied by fastened tissue segments "$T_1$", "$T_2$" when the respective surgical fasteners $130_A$, $130_B$, $130_C$ and retainers $200_A$, $200_B$, and $200_C$ are in their joined (engaged) formation. By altering the respective height (thickness) "$H_1$", "$H_2$", and/or "$H_3$" any desired level of hemostasis and blood flow in the fastened tissue segments "$T_1$", "$T_2$" may be effectuated. Other various attributes of the tissue (e.g., thickness or the presence of scar tissue) may increase or diminish the level of hemostasis and blood flow in the fastened tissue segments. It should be appreciated that portions of the retainer 200 extending from the backspan in which the apertures 206 are formed (the "aperture portion" of the backspan) have a thickness N (see FIG. 9).

Retainer 200c includes backspan $202_C$ that extends towards apertures 206 (discussed above in conjunction with FIG. 5) and has a height "$H_3$". When the retainer $200_C$ and surgical fastener $130_C$ are joined (FIG. 10C) within tissue segments "$T_1$", "$T_2$", the surgical fastener $130_C$ and retainer $200_C$ will form an enclosure that has an overall tissue compression space $140_C$ (FIG. 10C). Compression space or zone $140_C$ provides minimal blood flow restriction when the tissue segments are fastened together.

Retainer $200_B$ includes backspan $202_B$ that extends towards apertures 206 and has a height "$H_2$". When the retainer $200_B$ and surgical fastener $130_B$ are joined (FIG. 10B) within tissue segments "$T_1$", "$T_2$", the surgical fastener $130_B$ and retainer $200_B$ will form an enclosure that has an overall tissue compression space $140_B$ (FIG. 10B). The compression space $140_B$ is less than the compression space $140_C$ of fastener $130_C$. Accordingly, because the pressure exerted on the tissue segments "$T_1$", "$T_2$" by retainer $200_B$ and surgical fastener $130_B$ is greater than the pressure exerted on the tissue segments "$T_1$", "$T_2$" by surgical fastener $130_C$, the blood flow through the tissue surrounding surgical fastener $130_B$ will be less (more restricted) than the blood flow through the tissue surrounding surgical fastener $130_C$, thereby further facilitating hemostasis. However, because blood flow is not completely restricted through tissue compression space $140_B$, unnecessary necrosis of the fastened tissue may be prevented and/or impeded. Note also that the thickness of the aperture portions of the retainer 200b is greater along a larger distance than the thickness of the aperture portions of the retainer 200c due to the increased backspan thickness/height.

Retainer $200_A$ includes backspan $202_A$ that extends towards apertures 206 and has a height "$H_1$". When the retainer $200_A$ and surgical fastener $130_A$ are joined (FIG. 10A) within tissue segments "$T_1$", "$T_2$", the surgical fastener $130_A$ and retainer $200_A$ will form an enclosure that has an overall tissue compression space $140_A$ (FIG. 10A). The compression space $140_A$ is less than the compression space $140_B$ of fastener $130_B$. Accordingly, because the pressure exerted on the tissue segments "$T_1$", "$T_2$" by retainer $200_A$ and surgical fastener $130_A$ is greater than the pressure exerted on the tissue segments "$T_1$", "$T_2$" by retainer $200_B$ and surgical fastener $130_B$, and retainer $200_C$ and surgical fastener $130_C$, the blood flow through the tissue surrounding retainer $200_A$ and surgical fastener $130_A$ will be less (more restricted) than the blood flow through the tissue surrounding surgical fasteners retainer $200_B$ and surgical fastener $130_B$ and the tissue surrounding retainer $200_C$ and surgical fastener $130_C$, thereby further facilitating hemostasis. Because blood flow is substantially and/or completely restricted through tissue compression space $140_A$, this results in further facilitating and effectuating hemostasis.

FIG. 11 illustrates the surgical fasteners $130_A$, $130_B$, and $130_C$ and their respective retainers $200_A$, $200_B$, and $200_C$ loaded within the cartridge 100 and anvil 500, respectively, of the assembly 1006 shown in FIGS. 1 and 4. The surgical fasteners $130_A$, $130_B$, and $130_C$ and their respective retainers $200_A$, $200_B$, and $200_C$ are each arranged within inner, middle, and outer rows of cartridge 100 and anvil (retainer supporting portion) 500 respectively. As noted, rows $128_A$, $128_B$, and $128_C$ of cartridge 100 and corresponding rows $428_A$, $428_B$, and $428_C$ of anvil 500 are each spaced laterally from the channel 122, on opposite sides thereof, such that the surgical fasteners $130_A$, $130_B$, and $130_C$, and retainers $200_A$, $200_B$, and $200_C$ will be deployed on opposite sides of the cut-line (not shown) created in the tissue upon fastening. That is, the retainers $200_A$ with the largest height (or thickness) backspan provide a greater compressive force as there is a shorter distance between their backspan and the backspan of the respective fastener, and in the illustrated embodiment are provided in the inner rows closer to the cut line. The retainers $200_B$ have a greater distance between their backspan and the backspan of the respective fastener and are provided on the outer rows (outboard of the rows of retainers $200_A$) where the tissue might be thicker as a result of clamping by the instrument jaws (anvil and cartridge). If a third row of fasteners $130_C$ is used in this embodiment, then the retainers of FIG. 10C with the smallest height backspan (largest compression space) would preferably be placed on the outermost row furthest from the cut line. By providing the rows of fasteners which provide greater tissue compression as you approach the cut line, a greater range of tissue thicknesses can be effectively sealed by the same cartridge. It should be appreciated however, that the retainers can be placed on other rows than the foregoing. Also, while the inner, middle and outer rows $128_A$, $128_B$, and $128_C$ of cartridge 100 and corresponding rows $428_A$, $428_B$, and $428_C$ of anvil 500 are shown as including the surgical fasteners $130_A$, $130_B$, $130_C$ and retainers $200_A$, $200_B$, and $200_C$, respectively, the present disclosure contemplates the inclusion of the fasteners and retainers in other rows or arrangement of any of the surgical fasteners $130_A$, $130_B$, and $130_C$ and their corresponding retainers $200_A$, $200_B$, and $200_C$, disclosed hereinabove, either exclusively, such that only a single surgical fastener and retainer, e.g., surgical fastener $130_A$ and retainer $200_A$, is present in a particular row, or in combination, such that a variety of surgical fasteners, e.g., surgical fasteners $130_A$, $130_B$, and $130_C$ and retainers $200_A$, $200_B$, and $200_C$ are present in on more of the rows.

In one particular embodiment, the outer rows $128_C$, intermediate rows $128_B$, and inner rows $128_A$ of cartridge 100, and outer rows $428_C$, intermediate rows $428_B$, and inner rows $428_A$ of anvil 500 are comprised solely of surgical fasteners $130_C$, $130_B$, and $130_A$ and their corresponding retainers $200_C$, $200_B$, and $200_A$, respectively, such that the flow of blood through the tissue immediately surrounding the cut-line (not shown) is substantially, if not completely, restricted by joined surgical fastener $130_A$ and retainer $200_A$, whereas the flow of blood through the tissue surrounding the intermediate and outer rows along the cut-line are less restricted by joined surgical fasteners $130_B$, $130_C$ and retainers $200_B$, $200_C$, respectively. Accordingly, the flow of blood is minimized in the tissue immediately adjacent the cut-line and is increased gradually as the lateral distance from the cut-line is also increased. Also by this arrangement, the retainers with the largest height backspan (retainers $200_A$), are closest to the cut line where the tissue is generally compressed to the greater extent and the retainers with the smaller height backspan are positioned in the outer rows where the tissue is thicker. It should be appreciated that the height of the backspans could be varied to accommodate tissue of different thicknesses and to control tissue compression by the fasteners.

Figure 7A:
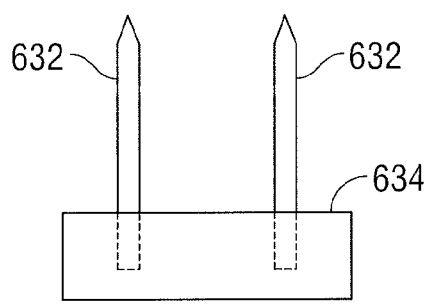
FIGS. 7A-7D illustrate different surgical fasteners that include different backspan configurations in accordance with alternate embodiments of the present disclosure.
Figure 7B:
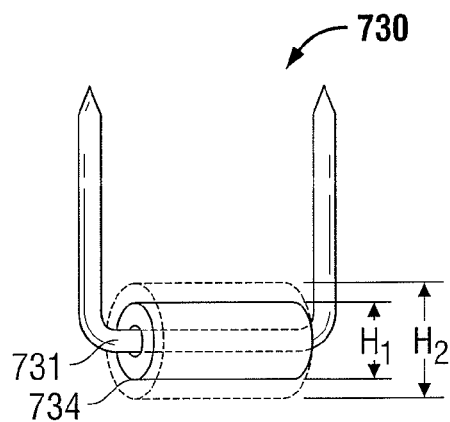
Figure 7C:
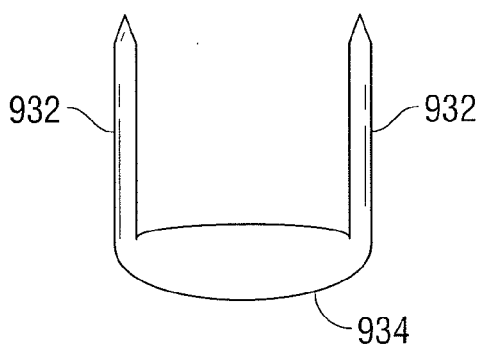
Figure 7D:
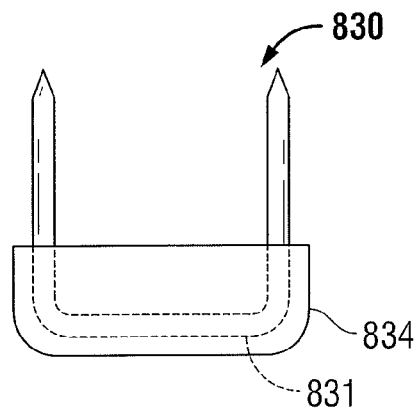

In the embodiments of FIGS. 7A-7D, various backspans of the surgical fastener are disclosed. In FIG. 7A, the backspan is an integral element 634 in which the fastener legs 632 are embedded. In FIG. 7C, the backspan 934 is integral with the fastener legs 932 and has a curved outer and inner surface. In the embodiments of FIGS. 7B and 7D, a separate backspan material is attached to the fastener 730, 830, respectively, with backspan 734 of FIG. 7B being in the form of a cylindrical collar encircling the backspan portion 731 of the fastener 730 and the backspan 834 of fastener 830 of FIG. 7D encompassing the backspan portion 831 of the fastener and a portion of the fastener legs 832. The backspan material of FIGS. 7B and 7D can be composed of thermoplastic overmolded onto the staple wire, by way of example. Varying the thickness or height of these backspans or backspan materials can vary the compressive force of the formed staple by varying the distance between the backspan of the fastener and the backspan of the retainer when engaged. FIG. 7B illustrates this by showing in phantom a collar of larger diameter to decrease the compression area when engaged with a retainer. Other backspan shapes and attachments to achieve the various compressive forces are also contemplated. It should be appreciated that varying height fastener backspans can be used with the varying height retainer backspans to vary the distance between the backspans to thereby vary the compression space and compressive force. It should also be appreciated that the varying height fastener backspans can be used with retainers of uniform height backspans to achieve the varying compression space and compressive force. (Varying height retainer backspans with uniform height fastener backspans were discussed in detail above).

From the foregoing and with reference to the various figure drawings, those skilled in the art will appreciate that certain modifications can also be made to the present disclosure without departing from the scope of the same. For example, the surgical fasteners described herein above may be formed from a variety of surgically acceptable materials including titanium, plastics, bio-absorbable materials, etc. Additionally, any of the aforementioned surgical fasteners may be treated, chemically or otherwise, prior to being loaded into cartridge 100.

It is also contemplated that the backspan 202 of the retainer 200 may include different configurations of tube, sleeve, collar, and/or grommet, such as those previously described with regard to the backspans of the surgical fastener.

Figure 12:
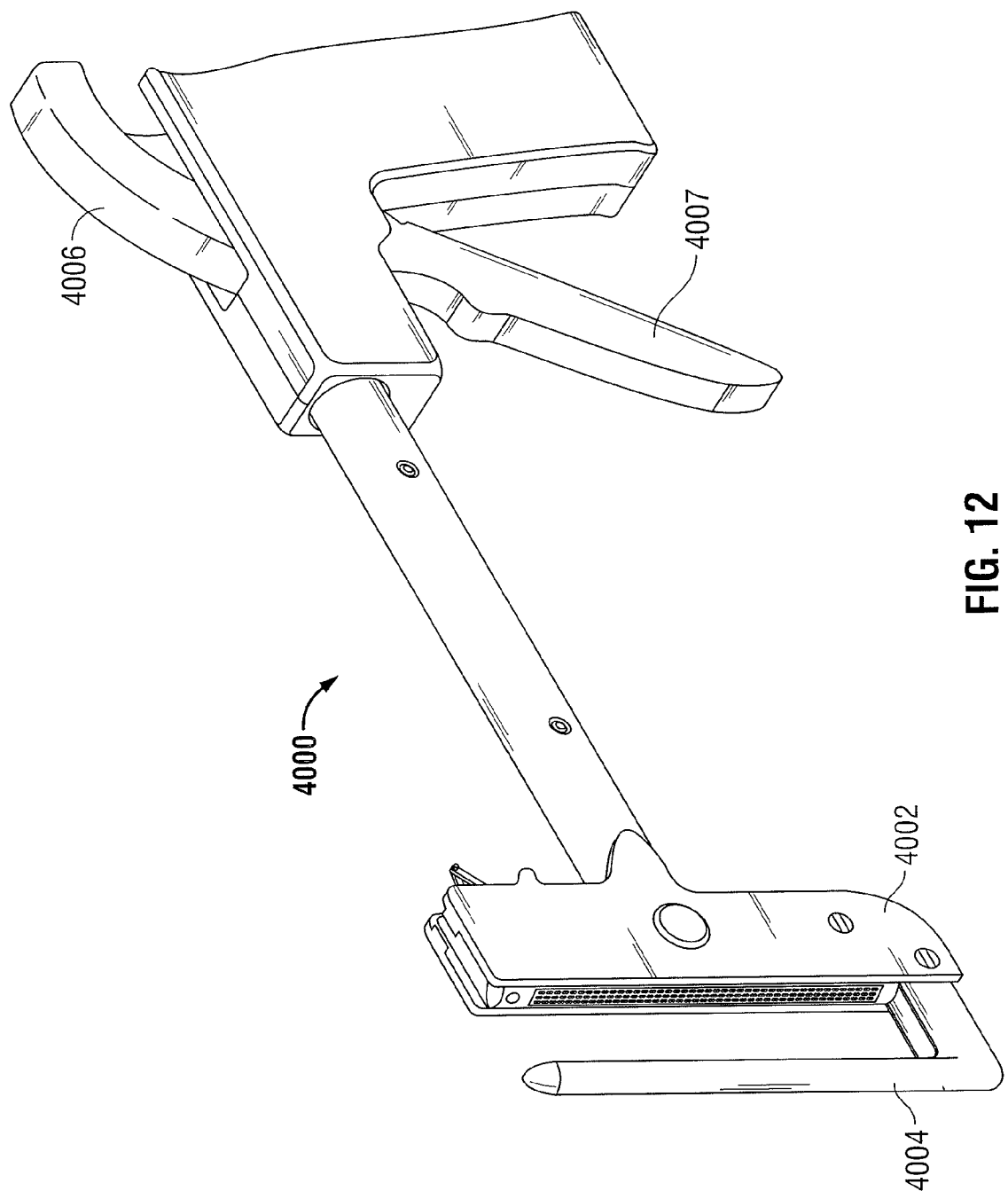
FIG. 12 illustrates another type of surgical fastener device that may employ an alternate embodiment of the surgical fastener cartridge in accordance with the present disclosure.

The fasteners and retainers of surgical fastening cartridge 100 and anvil may also be employed with a surgical fastener applying apparatus 4000 (FIG. 12) that is used to simultaneously deploy a plurality of surgical fasteners (surgical fasteners 130 and retainers 200 for example), arranged in substantially linear rows transverse to a longitudinal axis of the apparatus, into either side of a target section of tissue (not explicitly shown). Here, a scalpel or other such cutting element may be used to remove the target section of tissue, or a built in knife could be provided which could be advanced upon advancement (firing) of the fasteners. The fasteners 130 would be supported within the cartridge or fastener supporting portion 4002 and the retainers would be supported within the anvil or retainer supporting portion 4004. Approximation of the cartridge and anvil, e.g. linear movement of the fastener supporting portion 4002 toward the retainer supporting portion 4004, via movement of lever 4006 clamps tissue therebetween. The fasteners can then be advanced into the retainers as described above upon squeezing of handle 4007, providing varying compressive forces on the tissue due to the varying backspan heights. Further details regarding the use and function of surgical fastener applying apparatus 4000 may be obtained through reference to U.S. Pat. Nos. 7,070,083 and 5,964,394 the entire contents of which are incorporated by reference herein. In an alternate embodiment, the apparatus 4000 could include a cutting element as in the other cartridges disclosed herein. Such staplers can also include other mechanisms for approximating the anvil and cartridge and firing the fasteners. The cartridge and anvil can also be used with other apparatus for simultaneously deploying a substantially linear row of fasteners, such as U.S. Pat. No. 7,407,076, the entire contents of which is incorporated herein by reference.

As noted above, the fasteners and retainers of surgical fastening cartridge 100 and anvil 500 may also be employed with a surgical fastener applying apparatus 3000 (FIG. 3) that is used to sequentially deploy a plurality of surgical fasteners (surgical fasteners 130 and retainers 200 for example), arranged in substantially linear rows substantially aligned with the longitudinal axis of the apparatus, into either side of a target section of tissue (not explicitly shown). Here, a knife is advanced with the firing of the fasteners. The fasteners 130 would be supported within the cartridge or fastener supporting portion 3002 and the retainers would be supported within the anvil or retainer supporting portion 3004. The instrument halves 3001 and 3003 are clamped together to approximate the cartridge and anvil, and movement of firing knob 3005 sequentially fires the fasteners into engagement with the retainers as described above, providing varying compressive forces on the tissue due to the varying backspan heights.

As noted above, the fasteners and retainers of surgical fastening cartridge 100 and anvil may also be employed with a surgical fastener applying apparatus 2000 (FIG. 2) that is used to simultaneously deploy a plurality of surgical fasteners (surgical fasteners 130 and retainers 200 for example), arranged in substantially annular rows, into either side of a target section of tissue (not explicitly shown). Here, a knife is advanced with the firing of the fasteners. The fasteners 130 would be supported within the cartridge or fastener supporting portion 2002 and the retainers would be supported within the anvil or retainer supporting portion 2004. Approximation of the cartridge and anvil, e.g. retraction of the anvil 2004 by rotation of approximation knob (wing nut) 2005 clamps tissue between the anvil 2004 and cartridge 2002. The fasteners can then be advanced into the retainers as described above by squeezing of handles 2007, providing varying compressive forces on the tissue due to the varying backspan heights.

As described herein, differing compression spaces or zones are created by varying the height of the backspan of the retainers of the two-part fasteners. It is also contemplated as described above, that alternatively, the height of the backspans of the fasteners of the two-part fasteners can be varied to alter the compression spaces. Alternatively, as described above, both the height of the retainer backspan and the height of the fastener backspan can be varied to alter the compression spaces of the two part fasteners.

Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastener applying apparatus comprising a fastener supporting portion and a retainer supporting portion, the fastener supporting portion including a first row of first surgical fasteners and a second row of second surgical fasteners, the retainer supporting portion including a first row of first retainers and a second row of second retainers, the first fasteners engageable with the first retainers and the second fasteners engageable with the second retainers, the first fasteners each having a first fastener backspan and the second fasteners each having a second fastener backspan, and the first retainers each having a first retainer backspan disposed parallel to the respective backspan of the first fastener and having a first height, and the second retainers each having a second retainer backspan disposed parallel to the respective backspan of the second fastener and having a second height different from the first height of the first retainer backspan, wherein the fasteners and retainers are configured so when engaged a first distance between at least one of the first fastener backspans and respective first retainer backspan is different than a second distance between at least one of the second fastener backspans and respective second retainer backspan.

2. The fastener applying apparatus of claim 1, wherein the first row of fasteners is positioned inboard of the second row of fasteners and the first distance is less than the second distance.

3. The fastener applying apparatus of claim 2, further comprising a third row of third fasteners and a third row of third retainers, the third row of fasteners being positioned outboard of the second row of fasteners, the second distance being less than a distance between a backspan of at least one of the third fasteners and a backspan of a respective third retainer.

4. The fastener applying apparatus of claim 1, wherein the backspan of at least one of the first retainers has a greater height than the backspan of at least one of the second retainers, the first row of retainers being positioned closer to a central longitudinal axis of the retainer supporting portion than the second row of retainers.

5. The fastener applying apparatus of claim 4, further comprising a third row of third fasteners and a third row of third retainers, the third row of fasteners being positioned further from the central longitudinal axis than the second row of fasteners, and a height of a backspan of at least one of the third retainers is less than a height of the backspan of at least one of the second retainers.

6. The fastener applying apparatus of claim 1, wherein the retainer supporting portion and fastener supporting portion are pivotally attached.

7. The fastener applying apparatus of claim 1, wherein at least one of the retainer supporting portion and fastener supporting portion is movable along a substantially linear path to move the retainer supporting portion and cartridge supporting portion into approximation.

8. The fastener applying apparatus of claim 1, wherein the first and second rows of fasteners are arranged in a substantially annular configuration.

9. The fastener applying apparatus of claim 1, wherein the first and second rows of fasteners are arranged in a substantially linear configuration.

10. The fastener applying apparatus of claim 1, wherein the fasteners and retainers are composed of a bioabsorbable material.

11. The fastener applying apparatus of claim 1, wherein the fasteners have barbed tips.

12. The fastener applying apparatus of claim 1, wherein the fasteners have a pair of legs extending from the backspan and the retainers include a pair of apertures to receive legs of the respective fastener.

13. A surgical fastener applying apparatus comprising a fastener assembly having a first pair of first rows of fasteners and a second pair of second rows of fasteners and a corresponding first pair of rows of retainers and a second pair of rows of retainers to receive the respective fasteners, the first pair of rows of retainers having a backspan with a first height and the second pair of rows of retainers having a backspan with a second height different from the first height of the first retainer backspans, wherein at least one of the fasteners and retainers of the first pair of rows of fasteners and retainers is configured so when engaged applies a first overall compressive force on tissue and at least one of the fasteners and retainers of the second pair of rows of fasteners and retainers is configured so when engaged applies a second different overall compressive force on tissue.

14. The fastener applying apparatus of claim 13, wherein the first pair of rows of fasteners is positioned closer to a central longitudinal axis of the fastener assembly and the first compressive force is greater than the second compressive force.

15. The fastener applying apparatus of claim 13, wherein the fasteners have a backspan, and a distance between the fastener backspan and retainer backspan is less in at least one of the fasteners in the first fastener row than in at least one of the fasteners in a second fastener row.

16. A surgical fastener applying cartridge and anvil assembly for use with a surgical fastener applying instrument, the cartridge and anvil assembly comprising a cartridge having a first pair of rows of fasteners and a second pair of rows of fasteners and a retainer portion having first pair of rows of retainers and a second pair of rows of retainers to receive the respective fasteners, the first pair of rows of retainers having a backspan with a first height and the second pair of rows of retainers having a backspan with a second height different from the first height of the first retainer backspan, wherein at least one of the fasteners and retainers of the first pair of rows of fasteners and retainers is configured so when engaged applies a first overall compressive force on tissue and at least one of the fasteners and retainers of the second pair of rows of fasteners and retainers is configured so when engaged applies a second different overall compressive force on tissue.

17. The fastener applying cartridge and anvil assembly of claim 16, wherein the first pair of rows of fasteners is positioned closer to a central longitudinal axis of the cartridge assembly than the second pair of rows of fasteners and the first compressive force is greater than the second compressive force.

18. The fastener applying cartridge and anvil assembly of claim 17, wherein the fasteners have a backspan, and a distance between the fastener backspan and retainer backspan is greater in at least one of the fasteners and retainers in the second row of fasteners than a distance between at least one of the fasteners and retainers in the first row of fasteners and retainers.

* * * * *